(12) United States Patent
Timmons et al.

(10) Patent No.: US 7,597,016 B2
(45) Date of Patent: Oct. 6, 2009

(54) FUEL DEPOSIT TESTING USING BURNER-BASED EXHAUST FLOW SIMULATION SYSTEM

(75) Inventors: Suzanne A. Timmons, San Antonio, TX (US); Scott F. Timmons, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 100 days.

(21) Appl. No.: 11/556,479

(22) Filed: Nov. 3, 2006

(65) Prior Publication Data

US 2007/0186698 A1   Aug. 16, 2007

Related U.S. Application Data

(60) Provisional application No. 60/734,024, filed on Nov. 4, 2005.

(51) Int. Cl.
G01N 17/00 (2006.01)
G01N 31/12 (2006.01)
G01N 25/00 (2006.01)
G01N 21/12 (2006.01)

(52) U.S. Cl. ............... 73/865.6; 73/118.01; 73/866; 73/866.4; 374/45

(58) Field of Classification Search ......... 73/865.6, 73/866, 866.4, 37, 49.7, 114.69, 114.74, 73/114.77, 118.01–118.02; 250/341.6; 374/45, 374/57; 436/2, 9
See application file for complete search history.

(56) References Cited

U.S. PATENT DOCUMENTS

| | | | |
|---|---|---|---|
| 3,002,819 A | 10/1961 | Brace et al. | |
| 5,492,005 A | 2/1996 | Homan et al. | 73/61.62 |
| 5,693,874 A | 12/1997 | De La Cruz et al. | 73/61.62 |
| 5,942,682 A | 8/1999 | Ghetzler et al. | 73/147 |
| 6,370,946 B1 | 4/2002 | Lacey et al. | 73/61.62 |
| 6,568,255 B2 | 5/2003 | Pallozzi | 73/116.04 |
| 6,739,184 B2 | 5/2004 | Brazeau et al. | 73/116.02 |
| 7,140,874 B2 * | 11/2006 | Ingalls et al. | 73/118.01 X |
| 7,395,661 B2 * | 7/2008 | Iida | 60/297 |
| 7,412,335 B2 * | 8/2008 | Anderson et al. | 702/34 |
| 7,438,866 B2 * | 10/2008 | Iizuka et al. | 422/180 |
| 2001/0054281 A1 | 12/2001 | Adams et al. | 60/276 |
| 2003/0079520 A1 | 5/2003 | Ingalls, Jr. et al. | 73/23.31 |
| 2004/0007056 A1 | 1/2004 | Webb et al. | 73/114.77 |
| 2004/0025580 A1 | 2/2004 | Webb et al. | 73/118.01 |

(Continued)

OTHER PUBLICATIONS

"Stoichiometric Combustion", 1998, Taftan Data, http://www.taftan.com/thermodynamics/COMBUST.HTM, 1 page.*

(Continued)

Primary Examiner—Thomas P Noland
(74) Attorney, Agent, or Firm—Baker Botts LLP

(57) ABSTRACT

A method of using an exhaust flow simulation system to test the effects of exhaust system conditions on various materials. A typical exhaust flow simulator is a burner-based system, in which exhaust from burner combustion is exhausted through an exhaust line. A "test coupon" of the material may be placed at an appropriate location in the flow line, and tested to determine how it is affected by the exhaust resulting from various fuels and additives.

15 Claims, 2 Drawing Sheets

U.S. PATENT DOCUMENTS

| | | | |
|---|---|---|---|
| 2004/0216535 A1 | 11/2004 | Brostmeyer et al. | 73/865.6 |
| 2004/0237636 A1 | 12/2004 | Bartley et al. | 73/118.01 |
| 2005/0039524 A1 | 2/2005 | Ingalls, Jr. et al. | 73/114.77 |
| 2005/0042763 A1 | 2/2005 | Anderson et al. | 436/137 |
| 2008/0178574 A1* | 7/2008 | Webb et al. | 60/274 |
| 2008/0236134 A1* | 10/2008 | Krueger et al. | 60/39.182 |
| 2008/0295489 A1* | 12/2008 | Elfvik | 73/114.69 X |

OTHER PUBLICATIONS definition of Stoichiometric, The Free Dictionary by FARLEX. 2009, (viewed Jun. 24, 2009),http://www.thefreedictionary.com/Stoichiometric, 3 pages.*

International Search Report and Written Opinion PCT/US06/60516, 14 pages, Jun. 18, 2008.

Preliminary Report on Patentability PCT/US2006/060516, 6 pages, Jul. 24, 2008.

* cited by examiner

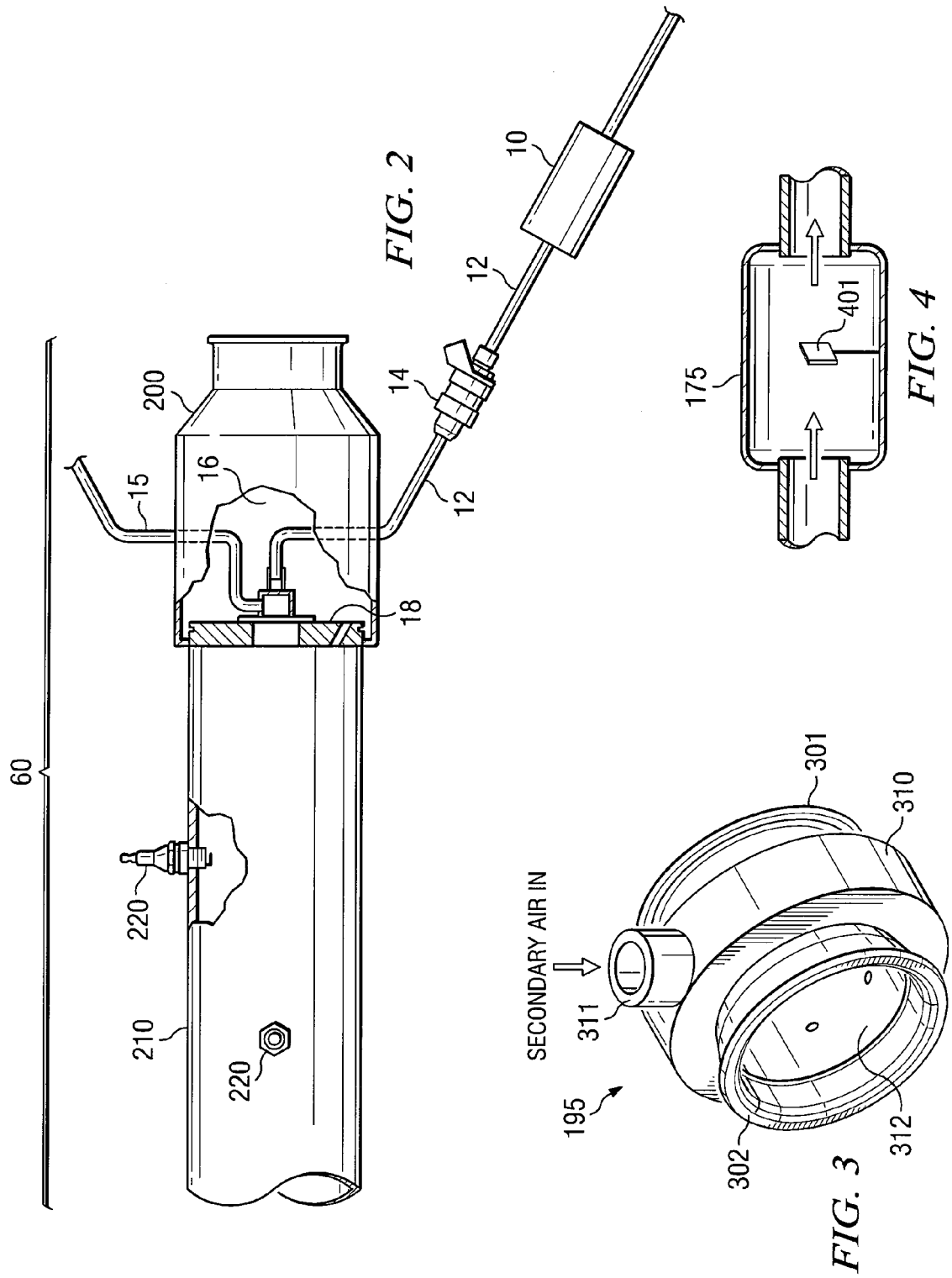

FUEL DEPOSIT TESTING USING BURNER-BASED EXHAUST FLOW SIMULATION SYSTEM

RELATED PATENT APPLICATION

This application claims the benefit of U.S. Provisional Application No. 60/734,024, filed Nov. 4, 2005 and entitled "Fuel Deposit Testing Using Burner Based Exhaust Flow Simulation System."

TECHNICAL FIELD OF THE INVENTION

The present application relates in general to systems for simulating the exhaust flow of an engine over extended driving conditions and high temperatures.

BACKGROUND OF THE INVENTION

As a result of stricter regulations for automotive emissions, it was desired to design a testing apparatus and procedure for testing emissions control devices. Historically, an actual internal combustion engine was used for such evaluations. However, the use of a real engine for long term testing can be inconsistent, maintenance intensive, and expensive to operate. In addition, a real engine does not conveniently permit the separate evaluation of individual variables, such as the effects of various constituents of fuel and oil.

U.S. Patent Pub. No. 2003/0079520, entitled "Method and Apparatus for Testing Catalytic Converter Durability" and U.S. Patent Pub. No 2004/0007056 A1, entitled Method for "Testing Catalytic Converter Durability", both describe an exhaust flow simulation system. The system comprises a fuel-combustive burner with an integrated, computerized control system. The system realistically simulates the flow of exhaust gas from an engine under a variety of load conditions.

BRIEF DESCRIPTION OF THE DRAWINGS

FIG. 2 illustrates the burner of the system of FIG. 1.

FIG. 3 illustrates the secondary air injector of FIG. 1.

FIG. 4 illustrates the interior of the test chamber of FIG. 1, with a test coupon placed therein.

DETAILED DESCRIPTION OF THE INVENTION

Figure 1:
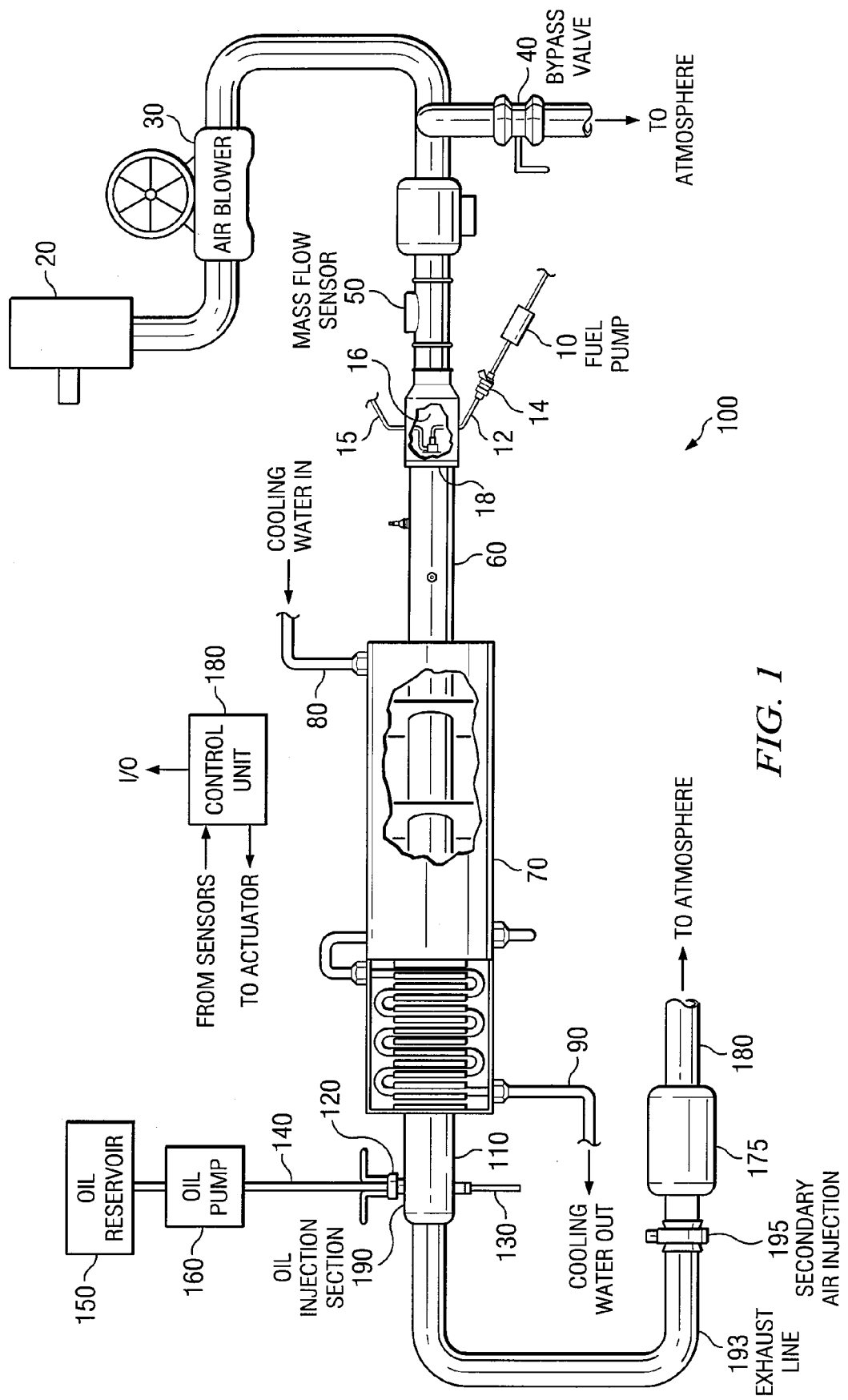
FIG. 1 illustrates an exhaust gas simulation system having a test chamber in accordance with the invention.

The following description is directed to a burner-based exhaust flow simulation system, which produces a flow of exhaust gas with a composition and temperature corresponding to those produced by the internal combustion engine of a motor vehicle. The system can be used with or without introducing oil to simulate engine oil consumption.

As an example of one application of an exhaust flow simulation system, an emissions control device can be installed on the exhaust line of the system. The effect of extended driving conditions and elevated temperatures on the emissions control device can be simulated. The system can also produce the effects of additives and contaminants from the engine fuel and lubricant oil on the durability of the emissions control device. The system is capable of "aging" the device, which can then be evaluated, and if desired, performance-tested on an actual vehicle.

Other applications of the exhaust flow simulation system are possible. Various sensors, such as those used for emissions monitoring and control, can be tested. Materials used to fabricate any component affected by exhaust gas can be tested. The subject of the testing may be a fuel, an additive, or an oil. Or, various environmental factors may be introduced and their effect evaluated.

The present invention is directed to the testing of the effects of the exhaust flow on a test material. The results of the testing can be evaluated to determine the suitability of the material for use in components that will be exposed to the exhaust gas of a production automobile or other engine-driven equipment. For example, after having been exposed to the simulated exhaust, the material can be examined for deposits, coking, corrosion, heat effects, and other symptoms of exposure to the exhaust flow.

U.S. Patent Pub. No. 2003/0079520 and U.S. Patent Pub. No 2004/0007056, referenced in the Background and incorporated by reference herein, each describes an exhaust flow simulation system with which the invention described herein may be used. However, the invention is not limited to those systems, and in general, can be applied to any burner-based exhaust flow simulation system.

FIG. 1 illustrates a burner-based exhaust flow simulation system 100 having a chamber 175 for materials testing in accordance with the invention. As explained below, system 100 is capable of separating the effects of fuel and oil, allowing precise control of each variable. It provides exhaust from combustion of gasoline or various other fuels, liquid or gaseous. The exhaust is generating under conditions of precise air to fuel ratio (AFR) control. The system has an oil atomization and injection subsystem provides definitive isolation of the effects of fuel and of lubricant at various consumption rates and states of oxidation. System 100 is capable of operating over a variety of conditions, allowing various modes of engine operation to be simulated, for example cold start, steady state stoichiometric, lean, rich, or cyclic perturbation.

System 100 has eight subsystems: (1) an air supply system to provide air for combustion to the burner, (2) a fuel system to provide fuel to the burner, (3) a burner system to combust the air-fuel mixture and provide the proper exhaust gas constituents, (4) a heat exchanger to control the exhaust gas temperature, (5) an oil injection system, (6) a secondary air injection system, (7) a materials testing chamber, and (8) a computerized control system.

Primary Air Supply System

An air blower 30 draws ambient air through an inlet air filter 20 and exhausts a pressurized stream of air. A mass air flow sensor 50 monitors air flow. The volume of air supplied is set by adjusting a bypass valve 40 to produce a desired flow rate of air.

The air blower 30, filter 20, and the mass air flow sensor 50 may be of any conventional design. An example of a suitable air blower 30 is an electric centrifugal blower.

Blower 30 may also be used for cooling system 100. For example, if the burner is off, system 100 may be rapidly cooled by using blower 30 to blow forced air on any part of system 100.

Fuel Supply System

A fuel pump 10 pumps engine fuel through a fuel line 12 to a fuel control valve 14. As used herein, the term "engine fuel" means any substance which may be used as a fuel for an internal combustion engine, including, but not necessarily limited to, synthetic gasoline, diesel, carbon-based liquefied fuel, methanol, or compressed natural gas.

An example of a suitable fuel control valve 14 is a solenoid valve that receives a pulse-width modulated signal from the control unit 180, and regulates the flow of fuel to the burner 60 in proportion to the pulse width. From the fuel control valve 14, the fuel is delivered to the fuel injector 16 associated with burner 60.

Burner

Burner 60 produces a desired combustion of the fuel and air. In the example of this description, burner 60 is a swirl-stabilized burner capable of producing continuous combustion at rich, lean, or stoichiometric air-fuel ratios.

FIG. 2 illustrates burner 60 in further detail. Burner 60 comprises a plenum chamber 200 and a combustion tube 210 separated by a swirl plate 18. The combustion tube 210 is constructed of material capable of withstanding extremely high temperatures. Preferred materials include, but are not necessarily limited to INCONEL or stainless steel, and optionally can have a window, made from a material such as quartz or other material that transmits IR, visible, or UV energy.

Air and fuel are separately introduced into the burner 60. Air from mass flow sensor 50 is ducted to the plenum chamber 200, then through the swirl plate 18 into the burner tube.

The swirl plate 18 is equipped with a fuel injector 16, implemented as an air-assisted fuel spray nozzle 16 at the center of the swirl plate 18. The swirl plate 18 has a central bore 255, and spray nozzle 16 is fitted to the swirl plate 18 at this central bore 255 using suitable means. Fuel from fuel supply line 14 is delivered to the spray nozzle 16, where it is mixed with compressed air from air line 15 and sprayed into the combustion tube 210. The compressed air line 15 provides high pressure air to assist in fuel atomization.

Swirl plate 18 is capable of producing highly turbulent swirling combustion, so as to provide a complex pattern of collapsed conical and swirl flow in the combustion area. The flow pattern created by the swirl plate 18 involves the interaction of a number of jets through swirl plate 18. The arrangement and angling of these jets dictate how they direct air. For example, "turbulent jets" may be used to direct the air toward the central bore. Other jets may be used to direct air from the outer circumference of the swirl plate 18. The precise dimensions and angular orientation of the jets may vary. The jets may further be used to prevent the flame from contacting the air assisted spray nozzle 16.

The swirling flow within tube 210 collapses and expands, preferably at intervals that are substantially equivalent in length to the inner diameter of combustion tube 210. In the example of this description, the inner diameter of the combustion tube 210 is 4 inches, and the intervals at which the swirling flow collapses and expands is every 4 inches.

Combustion tube 210 is equipped with several spark igniters 220. In a preferred embodiment, three substantially equally spaced igniters 220 are located around the circumference of the combustion tube in the gas "swirl path" created by the swirl plate 18. In a preferred embodiment these igniters 220 are marine spark plugs.

The swirl pattern within combustion tube 210 may be used to define the location of igniters 220 along the combustion tube 210. In the embodiment described herein, the igniters are located at first and second full expansions along the path of inner swirl jets.

Swirl plate 18 may be implemented as a substantially circular disc having a thickness sufficient to fix the air flow pattern and to create an "air shroud" that is effective to protect the fuel injector. In the example of this description, this thickness generally is about ½ inch or more. The swirl plate 18 is made of substantially any material capable of withstanding high temperature, a preferred material being stainless steel.

In some embodiments, suitable for combustion of low volatility fuels, the combustion tube 210 is further equipped with ceramic foam located downstream from the spray nozzle 16. Various materials may be used, preferably SiC ceramic foam.

Heat Exchanger

Referring again to FIG. 1, the exhaust from the burner 60 is routed to a heat exchanger 70. The heat exchanger 70 may be of any conventional design known to a person of ordinary skill in the art. In the example of this description, the heat exchanger 70 consists of two sections. An upstream section consists of a water jacketed tube. A downstream section is a vertical cross flow shell and tube heat exchanger. The vertical cross flow design minimizes steam formation and steam trapping within the cooling tubes. The heat exchanger 70 is provided with an inlet water line 80 and an outlet water line 90 which supply and drain cooling water. The heat exchanger 70 cools the exhaust gas to a temperature simulating that which is present at the inlet to an emissions control device 170.

Oil Injection System

Downstream from the burner 60, the exhaust gas is routed past an oil injection section 110, which may be used to introduce a precisely controlled amount of lubricating oil into the exhaust stream. In the example of this description, the oil injection section 110 is installed in a four inch diameter pipe.

The oil injection section 110 provides an atomized oil spray comprising oil droplets with a sufficiently small diameter to vaporize and oxidize the oil before it reaches the emissions control device 170. The oil injection system 110 may include means for metering the consumption rate and oxidation state (unburned, partially burned, or fully burned) of the oil delivered downstream the oil injection.

In operation, a sample of lubricant oil is withdrawn from an oil reservoir 150 by means of an oil pump 160. Substantially any type of pump may be used, preferably a peristaltic pump which feeds the oil from the reservoir through an oil injection line 140 and into a water cooled probe 120 from which the oil is injected into the exhaust gas.

Secondary Air Injection

Secondary air injector 195 is placed upstream of the emissions control device 170, and supplies air into the exhaust flow line 193. Although, this description is in terms of supplying air, injector 195 may be equivalently used to supply any other type of gas into the exhaust flow. One application of the secondary air injector 195 is to help control the composition or heat of the exhaust gas. For example, an injection of oxygen may be used to provide thermal excursions.

FIG. 3 is a perspective view, to illustrate secondary air injector 195 in further detail. A secondary air inlet 311 receives the secondary air, which is typically from a pressurized source. A hollow ring 310 has a solid outer wall 313 and a perforated inner wall 312, through which the air enters the exhaust line 193.

In the example of FIG. 3, air injector 195 is designed as an add-on part that can be installed into a gap in the exhaust line 193. Accordingly, it has bell-type sleeves 301 and 302 for snugly accepting ends of the exhaust pipe. Other means of attachment may be used. It possible to modify air injector 195 so that it is an integral part of exhaust line 193, such as by perforating a portion of exhaust line 193 with holes to form the inner wall 312 of secondary air injector 195.

In the example of this description, inner wall 312 has eight air injection ports 315. These air injection ports 315 are placed 22 degrees off center from the main air inlet 311 to help provide a even pressure distribution and to permit even air injection into the exhaust flow tube. The use of inner wall 312 with its multiple injection ports permits the pressured air to create a jet into the exhaust flow stream resulting in deeper penetration into the exhaust flow stream for better mixing.

If desired, the ports of inner wall 312 may be threaded to accept through-drilled set screws (not shown) at all eight injection locations. The set screws are the appropriate diameter to create deep penetration of the air jet perpendicular to the exhaust stream flowing up to 80 scfm or higher. The penetration depth may be changed by varying the diameter of the set screws.

In the example of this description, the air injection ports 315 are bored perpendicular to the surface of inner wall 312. Hence, the air enters perpendicularly to the exhaust flow. However, in other embodiments, they may be angled to provide higher turbulence resulting in better air distribution in the exhaust stream.

Downstream of secondary air injector 195, the exhaust gas, now mixed with the injected oil and secondary air, passes through an emissions control device 170, following which the exhaust gas is vented to the atmosphere.

Materials Testing Chamber

As stated above, in addition to testing actual emissions control devices installed on the exhaust flow line, system 100 can be used to test all sorts of materials and devices that may be exposed to the exhaust gas and/or its elevated temperatures. For example, a common problem in engines of all types is the buildup of deposits on valves. These deposits vary as a function of temperature, pressure, fuel type, and additives.

FIG. 4 illustrates the interior of test chamber 175, and how a sample of material 401 may be placed in test chamber 175 and exposed to the exhaust flow. Test chamber 175 permits fuels and fuel additives to be evaluated by examining deposits on test samples of materials placed in the exhaust flow stream.

The test material 401, also referred to herein as a "test coupon", may be placed at any appropriate location along the flow tube of system 100 to achieve the desired exhaust gas exposure and thermal experience. In FIG. 1, the location of test chamber 175 downstream of secondary air injector 195 is arbitrary—it may be placed anywhere in the exhaust stream downstream burner 60.

By placing a sample of material in the exhaust flow, different materials and coatings may be tested for various applications, such as intake and exhaust valve materials, valve seat materials, cylinder wall materials, and piston materials. The test coupon may be installed throughout a complete "aging" cycle, to determine long terms effects of the material. Various materials can be tested with various fuels, oils, and additives.

For example, thermal excursions may be achieved by controlling the stoichiometry of the exhaust gas and by injection of oxygen or other gases into the exhaust stream. The effect of high temperature and rapid temperature increases on the material may be evaluated. Blower 30 (or other cooling equipment) may be used to rapidly cool the system 100 or the exhaust itself, thereby permitting the effect of rapid temperature drops to be evaluated.

Test chamber may also be designed so that the sample is exposed to the spectral (UV, visible, or IR) energy of the burner flame. This spectral emission exposure may be controlled, such that testing involves multi-parameter control, with the parameters including spectral exposure as well as exposure to exhaust components and thermal conditions. If there are spectral effects on the material itself, the exhaust components, or thermal conditions, then the spectrally excited states and the effects on deposit formation can be tested at various areas within the flow line of system 100. Control of spectral effects can be accomplished by providing a controllable shield of the sample from the burner flame.

In other embodiments, the test sample need not be in direct contact with the exhaust gas flow. For example, a test for the effects of combustion could call for placing a test sample of material in burner 60 or upstream of burner 60. In the latter case, the exposure environment is that which a material would undergo in the intake portion of an engine. System 100 could also be equipped with an exhaust gas recirculation (EGR) path and a test sample placed in the flow line or the EGR path, such that the effects of recirculated exhaust on the sample may be tested.

Control Unit

Referring again to FIG. 1, control unit 180 receives input from various sensors associated with system 100 and delivers control signals to its various actuators. Control unit 180 may be implemented with conventional computing equipment, including processors and memory. It is equipped with suitable input devices, a monitor, and a multi-function data acquisition card, connected to an digital relay module to monitor and record system information, and to control system electronics. Control unit 180 is programmed to run various simulation programs.

The sensors include sensor 50 and may further include sensors for measuring various gas contents and flows. Various measured parameters collected by control unit 180 may include: the mass air flow in the system, the air/fuel ratio (linear and EGO), the exhaust gas temperature at the outlet from the heat exchanger, the exhaust gas temperature at the inlet to the emissions control device, and the exhaust gas temperature at the outlet from the emissions control device, and various chemical constituents of the exhaust. The information measured by the sensors is transmitted by electronic signals to control unit 180, which measures all of the monitored parameters on a periodic basis and stores the measurement data in memory.

The actuators controlled by control unit 180 include the various injectors, pumps, valves, and blowers described above. More specifically, control unit 180 controls the air-to-fuel ratio by modulating the fuel delivered to the fuel injector 16 under either an open loop or closed loop control configuration. Control unit 180 further provides a means to control ignition, air assist to the fuel injector, auxiliary air, fuel feed, blower air feed, and oil injection. An example of a suitable control system would be a proportional integral derivative (PID) control loop.

Control unit 180 monitors system 100 for safety. For example, it may be used to verify that the burner is lighted and that the exhaust is within specified limits for both temperature and air to fuel ratio. The control unit 180 is programmed to identify and address failure modes, and to monitor and control system 100 to a safe shutdown if a failure mode is detected.

Interactive interface programming of control unit 180 permits an operator to develop and run various aging cycles. The operator can use control unit 180 to investigate the effects of exposure to various oils and other fuel contaminants or additives. The inlet temperature to the emissions control device 170 can be adjusted over a wide range of temperatures.

Control unit 180 may be used to switch power to the blowers and fuel pump, as well as control the air assisted fuel injectors, burner spark, oil injection, and auxiliary air. System temperatures, mass air flow for the burner air, and the burner air to fuel ratio are measured and converted to engineering units. The software program uses measured data to calculate total exhaust flow and burner air to fuel ratio, and to check conditions indicative of a system malfunction. The burner air to fuel ratio may be controlled as either open or closed loop, maintaining either specified fuel flow or specified air to fuel ratio. Air to fuel ratio control is achieved by varying the rate of fuel delivered to the burner. Whenever necessary, open loop control can be activated allowing the operator to enter a fixed fuel injector pulse duty cycle. Closed loop control can be activated in which the actual burner air to fuel ratio is measured and compared to the measured value of the air to fuel setpoint and then adjusting the fuel injector duty cycle to correct for the measured error.

The invention claimed is:

1. A method of using an exhaust gas simulation system to test the effect of exhaust flow on a material, comprising:
    selecting a target temperature;
    placing a burner along a flow line;
    placing a heat exchanger downstream the burner, the heat exchanger operable to cool exhaust from the burner;
    inputting air into the flow line upstream the burner;
    injecting fuel into the burner;
    wherein the amount of air and fuel are selected to provide a target combustion mode, the mode being from the group of: stoichiometric, lean, and rich;
    igniting the fuel in the burner thereby creating an exhaust flow downstream the burner;
    placing a test sample of the material in contact with at least a portion of the exhaust flow downstream the burner and the heat exchanger, and downstream convection effects from the burner;
    controlling the heat exchanger so that the exhaust gas in contact with the test sample has the target temperature; and
    exposing the test sample to the exhaust flow over time.

2. The method of claim 1, wherein the placing step is performed by placing the sample in a test chamber inline the flow line, such that exhaust gas flows past and contacts the sample.

3. The method of claim 1, wherein the placing step is performed to expose the sample to the spectral energy of a flame produced by the burner.

4. The method of claim 3, further comprising the step of controllably shielding the sample from the flame.

5. The method of claim 1, further comprising the step of injecting engine lubricant into the exhaust flow.

6. The method of claim 1, further comprising the step of injecting a secondary gas into the exhaust flow upstream the sample.

7. The method of claim 1, further comprising the step of controlling the temperature of the exhaust flow.

8. The method of claim 1, further comprising the step of controlling the pressure of the exhaust flow.

9. A burner-based exhaust gas simulation system, comprising:
    a flow line for receiving input air at an input end;
    a combustive burner along the flow line, the burner operable to burn fuel and emit exhaust gas into the flow line;
    a heat exchanger for cooling the exhaust gas from the burner;
    a test chamber along the flow line and downstream the burner and the heat exchanger, and downstream convention effects of the burner, for receiving the exhaust gas and for containing a sample of test material;
    an exhaust outlet for exhausting the exhaust gas from the test chamber; and
    a controller for controlling the heat exchanger to achieve a target temperature of the exhaust in the test chamber, and for controlling the amount of air and fuel delivered to the burner to achieve a target combustion mode, the combustion mode being selected from the group of: stoichiometric, lean, and rich.

10. The system of claim 9, further comprising a blower for cooling the sample.

11. The system of claim 9, further comprising an injection system for injecting a liquid into the flow line downstream of the burner.

12. The system of claim 9, wherein the test chamber receives the entire exhaust gas flow from the burner.

13. The system of claim 9, wherein the system has an exhaust gas recirculation (EGR) path, and wherein the test chamber is placed in the EGR path.

14. The system of claim 9, wherein the test chamber has a window for visible, UV, or IR communication with the flame produced by the burner.

15. The system of claim 14, further comprising a controllable shield for controlling the amount of visible, UV, or IR communication between the flame and the sample.

* * * * *